United States Patent
Ingimundarson et al.

(10) Patent No.: US 9,180,038 B2
(45) Date of Patent: Nov. 10, 2015

(54) WALKER HAVING HEIGHT ADJUSTMENT AND METHOD FOR DOING THE SAME

(75) Inventors: Arni Thor Ingimundarson, Ladera Ranch, CA (US); Arnar Kristjansson, Ladera Ranch, CA (US); Duane Romo, Aliso Viejo, CA (US)

(73) Assignee: OSSUR HF, Reykjavik (IS)

( * ) Notice: Subject to any disclaimer, the term of this patent is extended or adjusted under 35 U.S.C. 154(b) by 76 days.

(21) Appl. No.: 13/198,161

(22) Filed: Aug. 4, 2011

(65) Prior Publication Data

US 2012/0035520 A1 Feb. 9, 2012

Related U.S. Application Data

(60) Provisional application No. 61/370,925, filed on Aug. 5, 2010.

(51) Int. Cl.
A61F 5/01 (2006.01)

(52) U.S. Cl.
CPC .............. *A61F 5/0111* (2013.01); *A61F 5/0195* (2013.01)

(58) Field of Classification Search
CPC ........ A61F 5/0195; A61F 5/0111; A43B 3/26
USPC ................ 602/12, 16, 23, 27–29, 5; 128/882; 36/109, 110, 100, 1.5
See application file for complete search history.

(56) References Cited

U.S. PATENT DOCUMENTS

| | | | |
|---|---|---|---|
| 1,089,305 A * | 3/1914 | Baughman | 602/23 |
| 3,805,773 A * | 4/1974 | Sichau | 602/28 |
| 4,922,630 A | 5/1990 | Robinson | |
| 4,974,583 A * | 12/1990 | Freitas | 602/24 |
| 5,078,128 A | 1/1992 | Grim et al. | |
| 5,329,705 A | 7/1994 | Grim et al. | |
| 5,464,385 A | 11/1995 | Grim | |
| 5,520,627 A * | 5/1996 | Malewicz | 602/26 |
| 6,383,156 B1 * | 5/2002 | Enzerink et al. | 602/16 |
| 6,921,376 B2 | 7/2005 | Tweardy et al. | |
| 6,997,891 B1 | 2/2006 | Vecsey | |
| 7,198,610 B2 | 4/2007 | Ingimundarson et al. | |

(Continued)

FOREIGN PATENT DOCUMENTS

| DE | 2 140 459 | 8/1971 |
| WO | 2009/023094 A2 | 2/2009 |
| WO | 2010/070364 A1 | 6/2010 |

OTHER PUBLICATIONS

Ossur Product Catalog, 2009, pp. 37 and 38.

(Continued)

*Primary Examiner* — Victoria J Hicks
*Assistant Examiner* — Kari Petrik
(74) *Attorney, Agent, or Firm* — Workman Nydegger

(57) ABSTRACT

A walker having height adjustment, and a method of use thereof, generally includes a base. Length adjustable strut assemblies are provided to allow the walker to be converted between a fully extended configuration, a high top walker configuration, and a fully retracted, low top walker configuration, as well as to numerous configurations having incremental heights between the fully extended and the fully retracted configurations. Thus, a modular support is provided that can be used to provide different levels of immobilization and can be used for various therapeutic purposes, can accommodate different patient leg lengths with one device, and allows practitioners to carry a reduced inventory.

15 Claims, 5 Drawing Sheets

(56) References Cited

U.S. PATENT DOCUMENTS

| | | |
|---|---|---|
| 7,303,538 B2 | 12/2007 | Grim et al. |
| 7,513,881 B1 | 4/2009 | Grim et al. |
| 7,534,220 B2 | 5/2009 | Cormier et al. |
| 7,597,674 B2 | 10/2009 | Hu et al. |
| 2004/0019307 A1* | 1/2004 | Grim et al. .................. 602/27 |
| 2007/0293798 A1 | 12/2007 | Hu et al. |
| 2009/0287127 A1 | 11/2009 | Hu et al. |
| 2009/0287128 A1 | 11/2009 | Ingimundarson et al. |
| 2010/0010410 A1 | 1/2010 | Hu et al. |

OTHER PUBLICATIONS

International Search Report in corresponding International Application No. PCT/US2011/046691.

Chinese office action from Chinese Patent Application No. 201180038158.2, Jun. 18, 2014.

* cited by examiner

WALKER HAVING HEIGHT ADJUSTMENT AND METHOD FOR DOING THE SAME

CROSS REFERENCE TO RELATED APPLICATIONS

This application claims the benefit of priority of the filing date of U.S. provisional application Ser. No. 61/370,925, filed Aug. 5, 2010, the entire contents of which is incorporated by reference herein.

FIELD OF THE INVENTION

The present invention relates generally to the field of orthopedic or prosthetic devices and more particularly to a device for immobilization of the lower leg, such as an orthopedic leg mounted walker, having height adjustment, and a method for adjusting the height thereof.

BACKGROUND

One of the main purposes of orthopedic leg mounted walker or walking boots (collectively referred herein as a "walker") is to provide immobilization to the lower leg, in particular the foot and ankle, as well as to provide compression to the lower leg post fracture, sprain, or other injury, such as Achilles tendon rupture.

Currently different levels of immobilization can be achieved by using different types of walkers such as a low top walker (supporting struts having a lower height) and a high top walker (supporting struts having a higher height). One main difference between the two types of walkers is the height that is covered on the lower leg, where a high top walker is used for injuries such as tibia fractures and ankle sprains and a low top walker is used for more localized foot injuries. It is believed that the higher up the leg the walker reaches, the more immobilization of the lower leg, foot, and ankle is achieved.

Many orthotists and practitioners prescribe and dispense both low top and high top walkers, since they regularly see patients having both types of injuries discussed above. Further, since each walker type is provided in many sizes (for example 5 different sizes) to accommodate patients having different anatomical sizes, a significant inventory of both the low top and high top walkers must be stocked.

Additionally, when patients tear or rupture their Achilles tendon, a regular high top walker is used for immobilization of the lower leg, ankle, and foot, but a heel wedge is placed inside the walker to reduce the stress on the tendon and to place the foot in a pointed downward position (equinus position). This causes the calf to raise high up from the main body of the walker, thus reducing immobilization and causing a poor fit.

Foot size is used as a determining factor when sizing patients for a walker. Each walker size is height dependant; the larger the foot bed is on the walker, the taller the walker is as well. It is recognized that, however, some patients have large feet but short legs, such that a regular type walker may not provide an optimal fit.

In another observation, during the treatment protocol for a fracture/ankle sprain, different levels of immobilization are required throughout the healing process. Initially a patient's lower leg, foot, and ankle should be completely immobilized. In order to promote healing, the patient should gradually gain more mobilization in the foot and ankle Presently, this change in immobilization level must be carried out with different products.

It can be seen that a walker having height adjustment would provide numerous benefits and advantages over existing walkers. For example, the walker having height adjustment can be used in place of both the low top and the high top walker, thus providing a single orthopedic device to accomplish the immobilization goals that previously required two different types of walkers. Additional specific benefits will be appreciated from the discussion below.

SUMMARY

In view of the above discussion, exemplary embodiments of a walker having height adjustment are disclosed that provide a modular support that can be used to provide different levels of immobilization and can be used for various therapeutic purposes, can accommodate different patient leg lengths with one device, and allows practitioners to carry a reduced inventory.

In general the walker having height adjustment includes a base having lower strut supports integrally formed therewith or connected thereto, an insole, and an outsole. Attachment points for straps, such as D-rings, are provided at various locations on the walker. A liner, such as a soft goods support, can be provided to generally encircle a majority of the lower leg, ankle, and foot.

Strut assemblies are connected to or integrally formed with the lower strut assemblies. The strut assemblies are configured to allow the walker having height adjustment to be converted between a fully extended configuration, a high top walker configuration, and a fully retracted, low top walker configuration, as well as to numerous configurations having incremental heights between the fully extended and the fully retracted configurations.

When patients tear or rupture their Achilles tendon, and a heel wedge is placed inside the walker, the walker having height adjustment can be adjusted to a maximum height to accommodate the higher positioning of the calf as caused by the heel wedge. Thus, proper immobilization can be maintained, as well as a proper fit, even though the calf has been raised up by the heel wedge.

For patients having large feet and short legs, the walker having height adjustment can be utilized to provide a proper fit and proper immobilization, in contrast to a regular walker, which has a height dependent upon the footplate size.

Further, during the treatment protocol for a fracture/ankle sprain, a single walker having height adjustment can be utilized to provide the different levels of immobilization that are required throughout the healing process.

As an alternative to height adjustable strut assemblies, an assortment of different struts may be provided having different predetermined sizes and shapes. The predetermined sized struts are lockable in to the walker base and removable depending on different size requirements or strut shape requirements.

In yet another alternative, shells can be attached to the telescoping strut so as to convert the walker into a circumferential-type walker. A plurality of attachable shells secure to the struts and the walker base to provide circumferential-type support to the leg and ankle.

From the disclosed embodiments of a walker having height adjustment, a modular support is provided that can be used to provide different levels of immobilization and can be used for various therapeutic purposes, can accommodate different patient leg lengths with one device, and allows practitioners to carry a reduced inventory.

BRIEF DESCRIPTION OF THE DRAWINGS

These and other features, aspects, and advantages of the present invention will become better understood with regard to the following description, appended claims, and accompanying drawings where:

Figure 1:
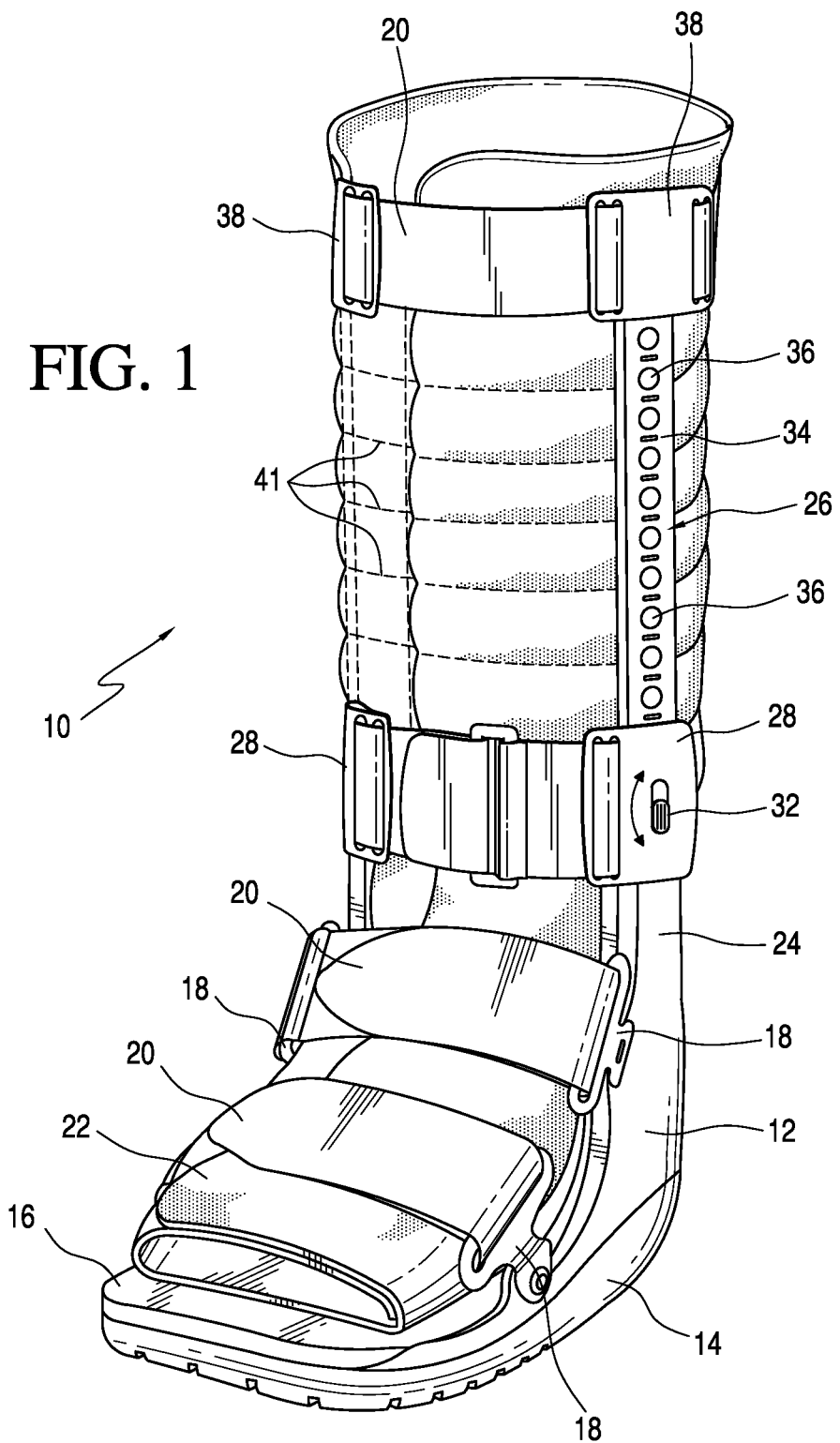
FIG. 1 is a front perspective view of an exemplary embodiment of a walker having height adjustment, shown in the fully extended position.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary embodiments of a walker having height adjustment and the components thereof, and in no way limit the structures or configurations of a walker having height adjustment and components thereof according to the present disclosure.

DETAILED DESCRIPTION

A. Environment and Context

Exemplary embodiments of a walker having height adjustment are provided for use in the immobilization of the lower leg, ankle, and foot following an injury and/or corrective surgery thereto. Features that are provided on one side of the device can easily be provided on the other side of the device. In this manner, it is intended that the exemplary embodiments of the walker having height adjustment described herein may be used on either right or left lower legs, with any appropriate reconfiguration of components that is deemed necessary for the proper fit and function of the device for the purpose of immobilization of either the left or right lower leg, ankle, and foot.

In the exemplary embodiments of the walker having height adjustment described herein, quick release strap mechanisms may be used to provide ease of securing and tightening the device to the lower leg. Exemplary quick release strap mechanisms are described in U.S. Pat. No. 7,198,610, granted April 2007, commonly owned, and herein incorporated in the entirety by reference.

The exemplary embodiments of the disclosure are adapted for immobilization of the lower leg, ankle, and foot of human beings, and may be dimensioned to accommodate different types, shapes and sizes of human joints and appendages.

Exemplary materials and configurations for components of the walker having height adjustment, such as sole portions and shell portions, are described in detail in U.S. Pat. No. 5,078,128, granted January 1992, U.S. Pat. No. 5,329,705, granted July 1994, U.S. Pat. No. 5,464,385, granted November 1995, and U.S. Pat. No. 7,303,538, granted December 2007, all commonly owned and incorporated herein in the entirety by reference.

For further ease of understanding the exemplary embodiments of an orthopedic device as disclosed herein, a description of a few terms is necessary. As used herein, the term "dorsal" has its ordinary meaning and refers to the top surfaces of the foot, ankle and foreleg or shin. As used herein, the term "plantar" has its ordinary meaning and refers to a bottom surface, such as the bottom of a foot. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and in fact they may break if bent with sufficient force. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties of support members or shells that provide support and are free-standing; however such support members or shells may have some degree of flexibility or resiliency.

B. Detailed Description of Exemplary Embodiments

Figure 2:
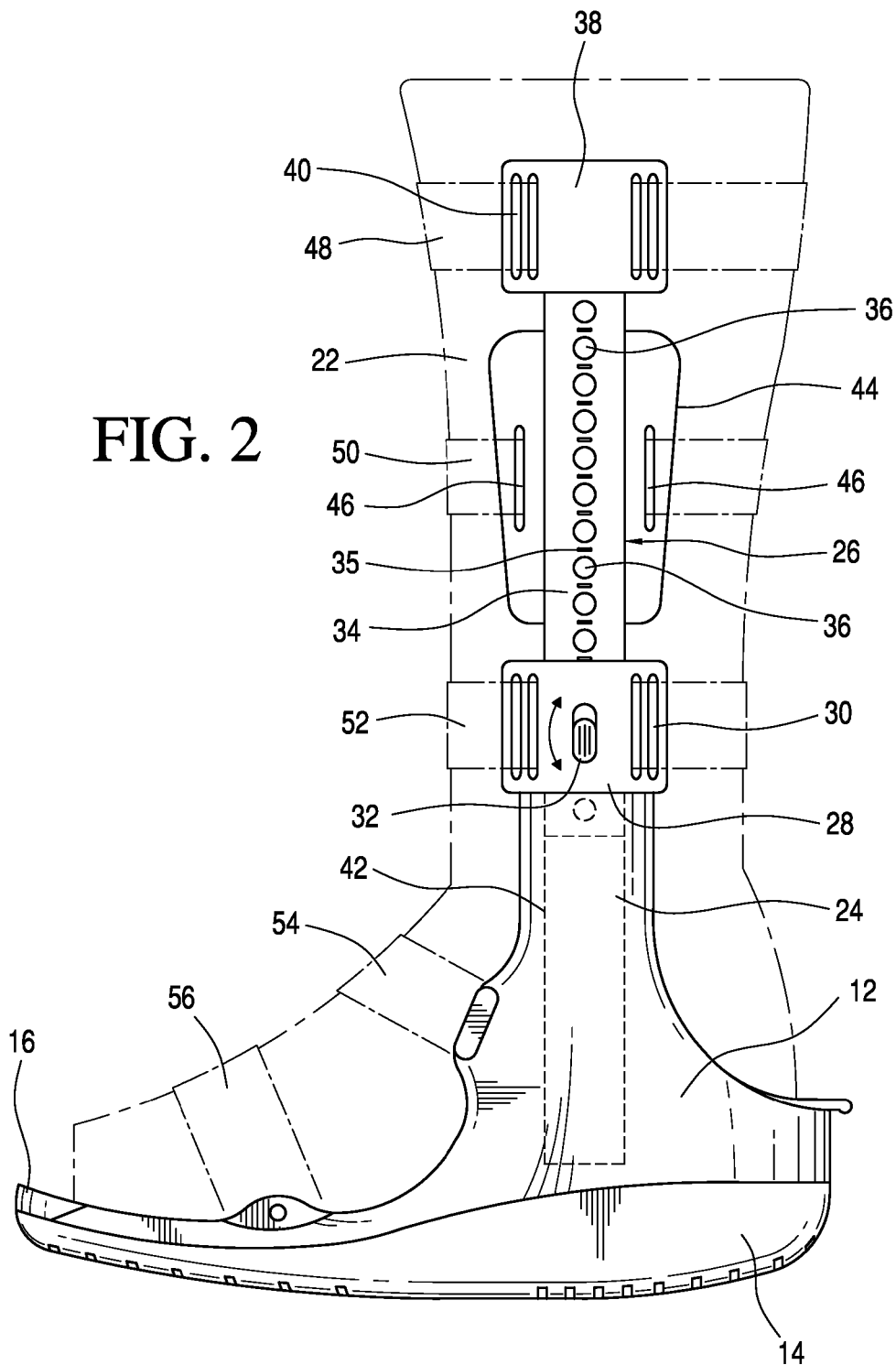
FIG. 2 is a side view of the walker having height adjustment according to FIG. 1, shown in the fully extended position.
Figure 3:
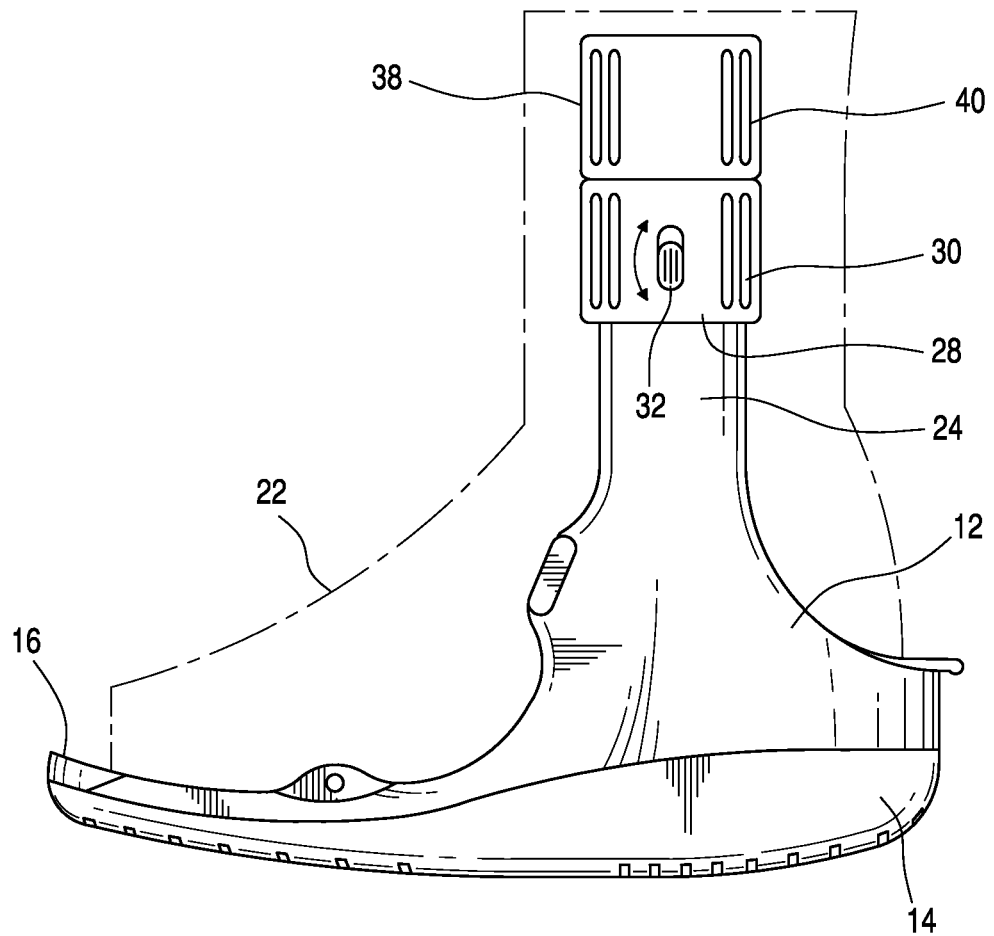
FIG. 3 is a side view of the walker having height adjustment according to FIG. 1, shown in the fully retracted, low top walker position.

An exemplary embodiment of a walker 10 having height adjustment is shown in FIGS. 1-3.

As best seen in FIG. 1, the walker 10 generally includes a base 12, which can be a rigid plastic or aluminum base, or can be made from any other suitable material. The base 12 also includes an outsole 14 formed therewith, either integrally, or separately. The outsole 14 can be any suitable configuration, such as a rubber sole having a roll over shape. An insole 16, such as a foam insert, is provided on the proximal surface of the base 12. The insole 16 can be formed from any suitable material, such as a viscoelastic foam or gel, in order to provide some cushioning for the patient's foot.

In order to retain the walker 10 on the patient's lower leg, and in order to provide the appropriate immobilization, a foam, soft good liner 22 is provided around the patient's lower leg, foot, and ankle. The liner 22 may also include an inflatable bladder provided therein in order to aid with providing compression and a proper fit of the walker 10. The liner 22 will be discussed in more detail below in relation to the fit of the walker having height adjustment.

Additionally, D-ring connecters 18, or any other suitable mechanism, can be provided on the walker base 12 in order to provide attachment points for straps 20, which are used to secure the walker 10 and the liner 22 to the patient's lower leg, ankle, and foot.

As seen in FIGS. 1-3, a lower strut support 24 is provided on each side of the walker base 12, with a space provided therebetween for the patient's foot. The lower strut supports 24 can be integrally formed with the base 12, or separately formed, and connected to the base 12 in any appropriate manner, such as, for example, with rivets, welding, brazing, adhesives. The lower strut supports 24 can be made from any suitable material, for example, the same material as the base 12. Other exemplary materials can include aluminum or other metal alloys, as well as carbon and/or glass fiber composite materials.

Attached to each of the lower strut supports 24 are strut assemblies 26. Each strut assembly 26 provides the mechanism to incrementally adjust the height of the walker 10. An exemplary configuration of the components of the strut assemblies 26 is described in detail in U.S. Pat. No. 7,534,220, granted May 19, 2009, commonly owned, and incorporated herein in the entirety by reference. The lower strut support 24 defines a receiving slot 42 into which the strut assemblies is inserted and retained to the walker base 12. The lower strut support 24 can be formed in a similar manner to the lower strut supports and corresponding slots described in U.S. Pat. No. 7,597,674.

In particular, each strut assembly 26 preferably includes a strut sleeve 28, which can be integrally formed with, or connected to, the lower strut support 24 in any suitable manner discussed above, or, for example, by a removable connection, such as nuts and bolts/machine screws. The strut sleeve 28 can be made from any suitable material, such as, for example, a molded plastic, or any other material discussed herein. Each strut sleeve 28 can be provided with suitable strap slots 30, or other strap connecting mechanism, such as D-rings, in order to accommodate straps 20 to secure the walker 10 to the patient's lower leg.

The strut sleeve 28 can have a generally rectangular cross-section with a rectangular channel, slot, or hole extending through the center. The rectangular channel, slot, or hole may also align with a similarly shaped channel, slot, or hole formed in the lower strut support 24, in order to provide an accommodating space for a strut extension 34 that is slidably received within the rectangular channel, slot, or hole. The slot or hole may be of any other suitable shape, corresponding to a complementary shaped strut extension 34.

It will be noted that the strut sleeve, strut assembly and slot formed by the walker base may have any number of cross-sectional shapes, including curved shapes.

Each strut extension 34 can be made from any suitable rigid material such as, for example, steel, plastic, aluminum, metal alloys, or carbon and/or glass fiber composites, and includes a series of spaced apart length-adjustment holes 36. If the strut extensions 34 are made from aluminum, they can be configured such that, by application of sufficient force, the strut extensions 34 may be slightly bent in order to accommodate different calf widths.

The strut assemblies 26 may have detents 35 formed thereon so as to provide an audible clicking sound as the strut extension 34 is adjusted in height relative to the lower strut support 24. These detents 35 may also serve as scoring on the strut extensions 34 to permit severing the strut extensions 34 so as to physically reduce the length of the strut assemblies 26.

The exemplary elongated flat plate shape of the strut extensions 34 allows the extensions to easily slide in and out of the respective strut sleeves 26 thereby adjusting the overall lengths of the strut assemblies 26 in order to adjust the operative height of the walker 10. It will be recognized that markings such as numerals, hash marks, and/or other indicia can be placed on the strut extensions 26 to guide and assist in repeatably and quickly setting up the desired length of the strut assemblies 26.

A selective locking mechanism, discussed in more detail below, allows the lengths of the strut assemblies 26 to be incrementally adjusted between numerous configurations of the walker 10. It will be noted that the strut assemblies may be provided without any length adjustment holes, and instead the strut sleeve is provided with a clamp mechanism instead of the lock lever so as to immovably secure the strut assemblies at floating lengths as opposed to the incremental adjustment described above in connection with the embodiment of FIG. 1.

For example, as shown in FIGS. 1 and 2, the strut assemblies 26 can be extended to their maximum length in order to provide support and immobilization, for example, when the walker 10 is used as a device to aid with healing of a torn or ruptured Achilles tendon. Thus, when a heel wedge is inserted with the insole 16, in contrast to a conventional walker, the calf of the patient's leg will be spaced far beyond the body of the walker, but instead, will be supported and immobilized by the strut assemblies 26, which are extended to their maximum length.

When the strut assemblies 26 are retracted to a length that is slightly less than the maximum extended length, the walker 10 can function in the manner of a high top walker.

In situations where patients have shorter legs, but large feet, the strut assemblies 26 can be adjusted to an appropriate height, shorter than the maximum extended length, such that the walker 10 can provide a comfortable fit, while maintaining proper immobilization.

In reference to FIG. 2, an expansion part 44 may be secured to the struts to embrace a greater portion of a wearer's leg, thereby distributing pressure on the patient's leg and providing means for securing a strap along the length of the strut assembly. The expansion part 44 may also include additional slots 46 that can accommodate a strap 50 adapted to extend in part or fully about a patient's leg. FIG. 2 also shows exemplary strap 48 secured to the proximal end of the strut assemblies 26, exemplary strap 52 secured to the strut sleeve 28, and straps 54 and 56 secured to the base. The expansion part can be secured to the length adjustment holes according to a variety of known fasteners, and be readily removable from the strut assembly.

As shown in FIG. 3, the strut assemblies 26 are retracted to their minimum length, such that the walker 10 can function in the manner of a low top walker. An even shorter height can be provided, if needed, by completely removing the strut extensions 34 from the strut sleeves 28, and/or by removing the strut sleeves from the lower strut supports 24.

Another advantage of the exemplary embodiment of the walker having height adjustment is that a single walker 10 can be utilized to provide modular support and immobilization throughout a treatment protocol that requires decreasing amounts of immobilization throughout the treatment process. To accomplish this, the height of the strut assemblies 26 can initially be set at or near the maximum extended height, and after predefined periods of time, or after appropriate amounts of healing, the height of the strut assemblies 26 can be decreased incrementally as needed, even until the minimum, fully retracted height of the strut assemblies 26.

Once the desired length of the strut extension 34 is determined and the strut extension 34 has been set at the desired length, a screw-in knob or lock lever 32 or similar actuating device, is turned, for example, 180 degrees clockwise manually to lock the strut extension 34 to the respective strut sleeve 28 thus inhibiting further relative sliding. To accomplish this, the screw-in knob or lock lever 32 can include a post extending underneath the lever and having threads thereon that engage threads in the sleeve 28 and that advance the post into one of the adjustment/receiving holes 36 of the respective strut extension 34.

The screw-in lever 32 preferably has a low profile, elongated lever-like shape so that via manual twisting action by the user, sufficient torque is generated to advance the post into the respective strut extension adjustment hole. A low profile prevents inadvertent operation of the screw-in lever by accidental brushing against, for example, clothing, the wearer's limb, or furniture. For better grip, the upper surface of the lever may be textured.

To unlock the strut extension 34 from the strut sleeve 28, an opposite turn of the screw-in lever 34 withdraws the post from engagement with the selected hole 36. The strut extension and its sleeve can now freely slide relative to each other.

To provide sufficient strength, the screw-in lever 32 and strut sleeves 28 can be made from glass filled nylon or like polymers. The strut sleeves 28 may have an aluminum, steel, or like metal skeleton over which the plastic is molded if more strength is desired.

The strut assembly may have additional securing means that engage the receiving slot in addition to securing to the strut sleeves by the screw-in lever. The means may include a hook assembly and the receiving slot can be formed in a similar manner as discussed in U.S. Pat. No. 7,303,538. This arrangement provides a two point securement to the walker by the strut assembly; the lock lever and the additional securing means.

A strut cuff 38 can be provided at the proximal end of the strut extension 34. The strut cuff 38 can be similarly formed like the strut sleeve 28, such that a channel or slot for receiving an end of the strut extension 34 is provided. Alternatively, the strut cuff 38 can be a plastic material integrally molded with or over the end of the strut extension 34. As a further alternative, the strut cuff 38 can be fixedly or removably connected to the end of the strut extension 34, utilizing appropriate mechanisms, such as those previously discussed. Like the strut sleeve 28, the strut cuff 38 can include strap slots, or other suitable connection mechanisms to retain straps 20 therewith.

Turning to the liner 22, one liner having a size suitable for use with the walker 10 in the fully extended position can be provided. When the liner 22 is constructed of foam, and has no inflatable bladder, the liner 22 can be trimmed as needed as the height of the walker is decreased, so that the liner 22 does not extend far beyond the strut cuffs 38. It is contemplated that if the liner includes a bladder, the bladder can be appropriately segmented, such that the liner with the inflatable bladder can be similarly trimmed.

As a further alternative, and as generally shown in FIG. 3, the liner 22 may be provided in two parts, a foot part and a calf part, which may simply be a foam strap, such that when the walker 10 is in the fully retracted configuration, only the foot part is utilized, and the calf part can be removed. If two liner parts are provided, each liner part may include a distinct inflatable bladder.

FIG. 1 shows how the liner 22 may be quilted to facilitate the trimming of the liner according height reductions of the strut assemblies relative to the walker base. The quilted structure may be formed by generally circumferential stitching 41 allowing for the liner to be trimmed without significant fraying of the liner since the height settings of the liner are compartmentalized by the circumferential stitching. Of course, the liner is not to be limited to quilting for facilitating height reduction; any means known to the skilled person in orthopedics or textiles is envisioned for being included for use in the walker embodiments discussed herein to accommodate height reduction of the liner.

While one exemplary configuration of a mechanism for locking the strut extension 34 at a specific height is described, it will be recognized that other suitable mechanisms can also be provided. For example, instead of locking holes provided on the strut extension 34, protrusions may be positioned along the length of the strut extension 34 for selective engagement with a respective opening or openings in the strut sleeve 28.

Figure 5:
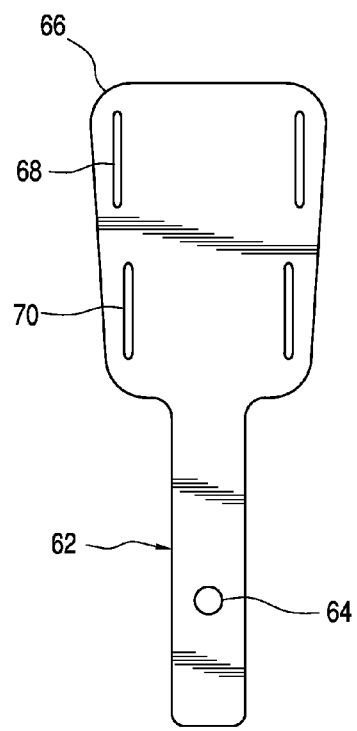
FIG. 5 is an exemplary view of strut having a predetermined shape and size for securing to the walker base of FIG. 4.
Figure 4:
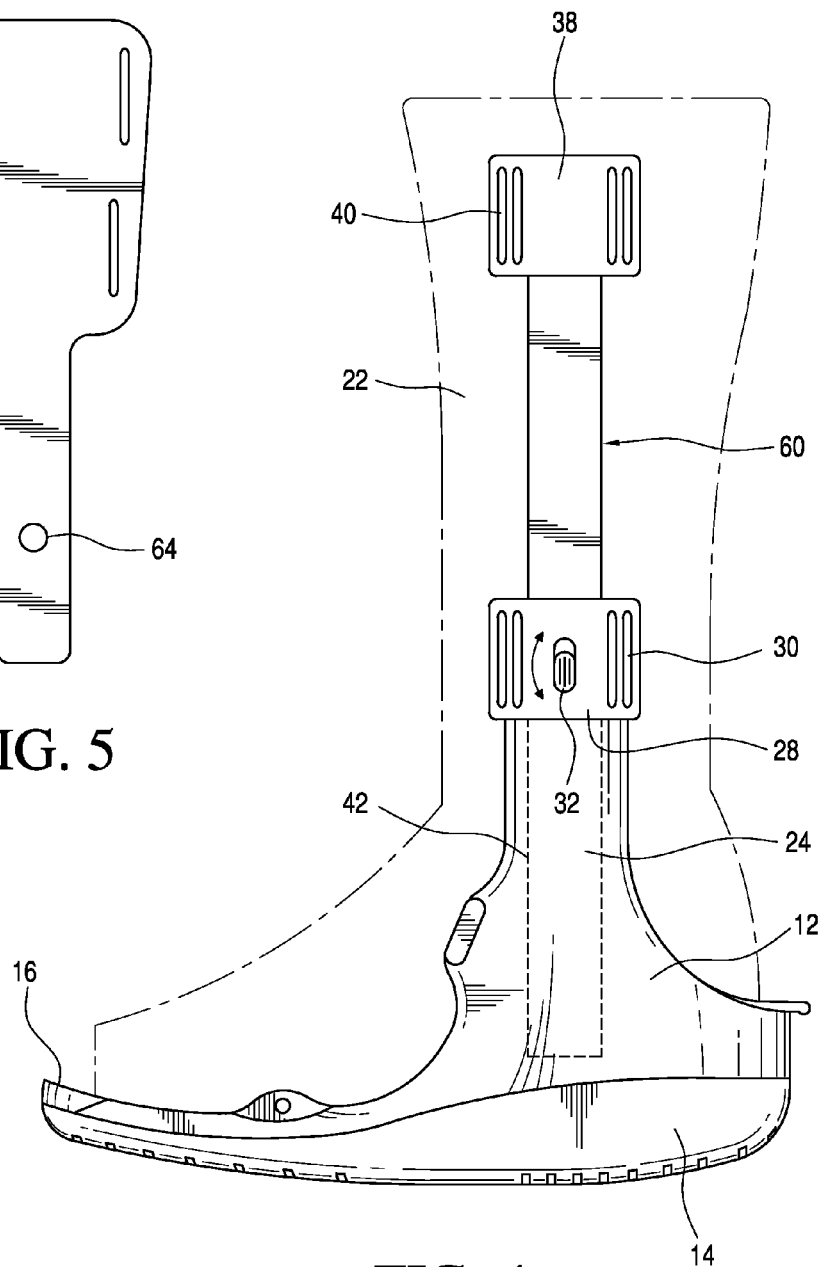
FIG. 4 is a side view of another walker embodiment showing a strut having a predetermined length secured into a walker base.

In the embodiments of FIGS. 4 and 5, the strut assembly 60 is pre-sized and lacks the adjustable height settings in the embodiments of FIGS. 1-3. While the strut assembly 60 is removable from the receiving slot 42 formed in the lower strut support 24, yet lockable by the lock lever 32 to be removably secured within the receiving slot 42.

FIG. 5 shows how a differently shaped and sized strut assembly 62 can be inserted into the receiving slot 42 of the lower strut support 24 and removably retained thereby. This strut has a wider and proximal end 66 and defines a couple of rows of openings 68, 70 for receiving straps. A locking opening 64 is provided at the distal end of the strut 62 for securing to the lock lever 32.

The strut assembly 62 can be used to replace the strut assembly 60 to provide for greater proximal support and additional strapping capabilities. The embodiment of FIG. 5 is just one of many available configurations for strut assemblies that can be used with the walker. It is envisioned that a practitioner can store a variety of different types of strut assemblies that can be used for differently sized patients and according to different needs such as enhanced strapping capabilities and a greater surface area for distributing pressure over the patient's leg.

Figure 6:
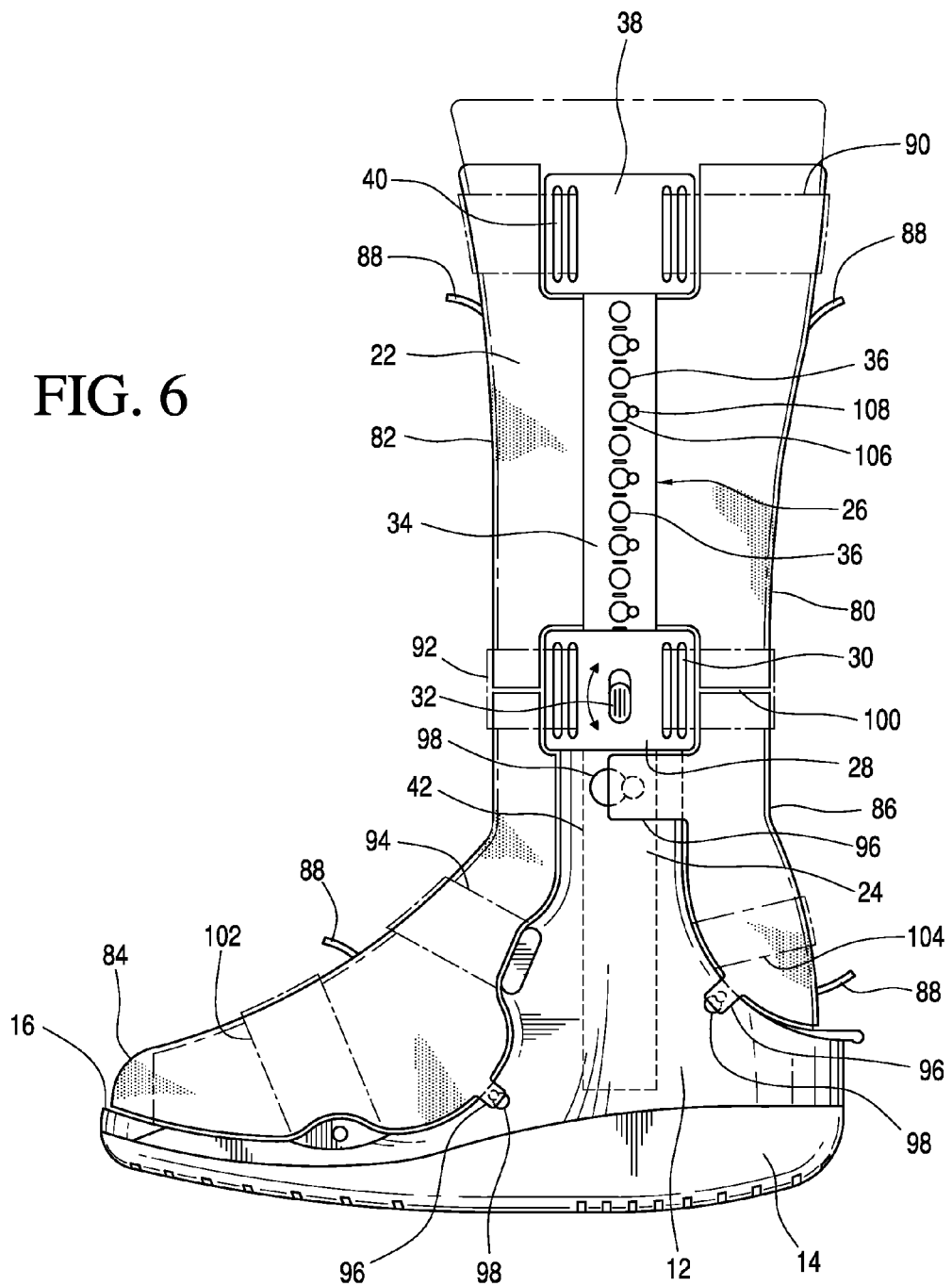
FIG. 6 is a side view of another walker embodiment showing the walker of FIG. 1 converted into a circumferential-type walker.

In the embodiment shown in FIG. 6, the walker of FIG. 1 is converted into a circumferential-type walker having a circumferential shell assembly. An example of a circumferential-type walker is described in U.S. patent application publication no. 2009/0287127. A posterior shell 80 is removably secured to the strut assembly 26 by attachments 96. While the attachments 96 may be a variety of different types, FIG. 6 shows the attachments as key hole slots 106 formed by the length adjustment holes 36, whereby pin heads 108 engage the key hole slots 106. The posterior shell 80 may be trimmable so as to allow for height adjustment according to the height settings of the strut assembly.

A distal anterior base shell 84 secures to the walker base 12 as well as a distal posterior base shell 86 removably connect to the walker base 12. The distal anterior and posterior base shells 84, 86 secure to the walker base 12 by tabs 96 formed on the anterior and posterior base shells via key hole attachments 98. The distal and posterior base shells 84, 86, combine with the posterior shell 80 to form a generally continuous structure other than gaps 100 formed therebetween to account for the various fits to the walker base and strut assemblies.

A dorsal shell or anterior shell 82 interfits with the posterior shell 80 and the distal anterior base shell 84, in a similar manner as described in U.S. patent application publication no. 2009/0287127. Straps 90, 92, 94, 102 retain the dorsal shell 82 to the posterior shell 80 and the distal anterior base shell 84. A strap 104 may extend above the distal posterior base shell 84. The anterior shell may be trimmable much in the same manner as the posterior shell.

Each of the posterior shell 80, anterior shell 82, distal anterior base shell 84 and distal posterior base shell 86 form the circumferential shell assembly. These shells may each have a bladder secured to their interior surface so as to provide means for adjusting the pressure about the patient's leg. Suitable fluid transfer means for the bladders extend from the shells in the form of tubes 88.

Any of the shells of the circumferential shell assembly may be secured to either an exterior or interior surface of the walker base and strut assembly.

Alternatively, other exemplary mechanisms that may be used to adjust and set the length of the strut extension 34 are described in U.S. Pat. No. 6,921,376, granted Jul. 26, 2005, and U.S. Pat. No. 7,513,881, granted Apr. 7, 2009, both commonly owned and incorporated herein in the entirety by reference. Another alternative length adjustment mechanism that may be used is described in detail in U.S. Pat. No. 6,383,156, granted May 7, 2002, and incorporated herein in the entirety by reference.

C. Conclusion

It will be recognized that the walker having height adjustment and components thereof can be made from any suitable materials.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features from the disclosed embodiments and variations. In addition to variations described herein, other known equivalents for each feature can be mixed and matched by one of ordinary skill in this art to construct a walker having height adjustment in accordance with principles of the present invention.

Although this invention has been disclosed in the context of exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. A walker having height adjustment, comprising:
   a base including an outsole having a roil over shape and an insole provided along an inside surface of the base for receiving a foot; and
   at least one adjustable length strut assembly connected to the base; wherein the walker can be converted between a fully extended configuration and a fully retracted configuration, as well as to numerous configurations having a plurality heights between the fully extended and the fully retracted configurations, the at least one strut assembly including a strut extension;
   a lower strut support extending upwardly from the base, the lower strut support forming a receiving slot for slidably receiving the strut extension therein, the lower strut support integrally formed with the base and a same material forming the base;
   a strut sleeve connected to a top surface of the lower strut support and defining a slot corresponding to the receiving slot of the lower strut support for slidably receiving the strut extension therein, and the strut sleeve including at least one strap connecting mechanism;
   a strut cuff provided at a proximal end of the strut extension;
   wherein the strut extension generally extends a maximum extended length from the receiving slot in the fully extended configuration such that the maximum extended length is defined as a segment of the strut extension extending beyond the strut sleeve and outside of the lower strut support including a portion extending within the strut sleeve, and the strut extension extends within the receiving slot a distance that is slightly less than the maximum extended length in the fully retracted configuration such that the strut cuff and the strut sleeve abut one another.

2. The walker according to claim 1, wherein the strut extension defines a plurality of incremental length adjustment openings along the length for permitting selective incremental adjustment of the strut assembly relative to the lower strut support.

3. The walker according to claim 1, wherein the strut sleeve includes a lock device arranged to engage and secure the strut assembly to the base.

4. The walker according to claim 3, further comprising an actuating device arranged for locking the lock device to the strut assembly.

5. The walker according to claim 1, further comprising a liner arranged for size adjustment according to the height adjustment of the strut assembly relative to the base wherein the liner defines a quilted structure formed from a plurality of circumferential stitching along the height of the liner.

6. The walker according to claim 1, further comprising an expansion part securable to the strut assembly at a plurality of locations along the height of the strut assembly.

7. The walker according to claim 6, wherein the expansion part defines at least one opening for receiving a strap.

8. The walker according to claim 1, further comprising at least two strut assemblies having a predetermined size, and having different shapes relative to one another, each of the at least two strut assemblies having a different height relative to one another and removably securing to the base.

9. The walker according to claim 1, further comprising a circumferential shell assembly removably securable to the strut assembly and the base.

10. The walker according to claim 1, wherein the strut extension defines a plurality of detents to provide an audible clicking sound as the strut extension is adjusted in height relative to the lower strut support.

11. The walker according to claim 1, wherein the strut extension has an elongated flat plate shape.

12. A method of adjusting a height of a walker having height adjustment, the method comprising:
   providing a base and a lower strut support extending upwardly from the base, the lower strut support including a slot for slidably receiving a strut extension therein, the lower strut support integrally formed with the base and a same material forming the base, and at least one adjustable length strut assembly having the strut extension defining a length slidably connected to the base by the lower strut support defining the slot, a strut cuff provided at a proximal end of the strut extension and a strut sleeve connected to the lower strut support; and
   adjusting the length of the at least one adjustable length strut assembly in order to convert the walker between a fully extended configuration and a fully retracted configuration, as well as to numerous configurations having different heights between the fully extended and the fully retracted configurations;

wherein the strut extension generally extends a maximum extended length from the receiving slot in the fully extended configuration such that the maximum extended length is defined as the segment of the strut extension extending beyond the strut sleeve and outside of the lower strut support including a portion extending within the strut sleeve, and the strut extension extends within the receiving slot a distance that is slightly less than the maximum extended length in the fully retracted configuration such that the strut cuff and the strut sleeve abut one another;

further comprising the step of locking the strut assembly in a fixed location relative to the base, the walker including the strut sleeve connected to a top surface of the lower strut support and defining a slot corresponding to the slot of the lower strut for slidably receiving the strut extension therein, and at least one strap connecting mechanism, the strut sleeve including a lock device arranged to engage and secure the strut assembly to the base.

13. The method according to claim 12, further comprising the step of adjusting straps according to the adjusted length of the strut assembly.

14. The method according to claim 12, wherein the walker includes a liner, the method further comprising the step of adjusting the height of the liner according to a selected adjusted height of the strut assembly.

15. The method according to claim 12, further comprising the steps of selecting at least two adjusted heights of the strut assembly, a first selected adjusted height of the strut assembly being locked in place, and a second selected adjusted height of the strut assembly being selected and locked in place after the first selected adjusted height is obtained.

* * * * *